(12) United States Patent
Stewart et al.

(10) Patent No.: US 6,833,255 B1
(45) Date of Patent: Dec. 21, 2004

(54) DROSOPHILA MELANOGASTER P70 S6 KINASE

(75) Inventors: Mary Stewart, Fargo, ND (US); Sara Kozma, Hesingue (FR); George Thomas, Hesingue (FR)

(73) Assignee: Novartis, AG, Basel (CH)

( * ) Notice: Subject to any disclaimer, the term of this patent is extended or adjusted under 35 U.S.C. 154(b) by 0 days.

(21) Appl. No.: 10/355,724

(22) Filed: Jan. 31, 2003

Related U.S. Application Data

(62) Division of application No. 09/817,310, filed on Mar. 26, 2001, now Pat. No. 6,534,311, which is a continuation of application No. 09/230,247, filed as application No. PCT/EP97/03680 on Jul. 11, 1997, now abandoned.

(30) Foreign Application Priority Data

Jul. 24, 1996 (GB) .............................................. 9615498

(51) Int. Cl.$^7$ .......................... C12P 21/06; C12N 1/20; C12N 5/00; C07H 21/02; C07K 1/00
(52) U.S. Cl. .............. 435/69.1; 435/252.3; 435/254.11; 435/320.1; 435/325; 435/410; 435/455; 536/23.1; 536/23.2; 536/23.5; 530/350
(58) Field of Search .............................. 435/69.1, 320.1, 435/325, 455, 252.3, 254.11, 410; 536/23.1, 23.2, 23.5; 530/350, 351

(56) References Cited

FOREIGN PATENT DOCUMENTS

| EP | 0239400 | 3/1987 |
|---|---|---|
| WO | WO 9007861 | 7/1990 |

OTHER PUBLICATIONS

Banerjee, et al., Proc. Natl. Acad. Sci. USA, "Molecular Structure of a Major Insulin/Mitogen–activated 70–kDa S6 Protein Kinase", vol. 87, pp. 8550–8554 (1990).
Baumgartner, et al., Genes & Dev., "Structure of Two Genes at the Gooseberry Locus Related to the Paired Gene and Their Spatial Expression During Drosophila Embryogenesis", vol. 1, pp. 1247–1267 (1987).
Blenis, et al, Proc. Natl. Acad. Sci., "Signal Transduction Via the Map Kinases: Proceed at Your Own RSK", vol. 90, pp. 5889–5892 (1993).
Chen, C.A. & Okayama H., BioTechniques, vol. 6 (7), "Calcium Phosphate–Mediated Gene Transfer: A Highly Efficient Transfection System for Stably Transforming Cells with Plasmid DNA," pp. 632–638 (1998).
Chung J. et al., Nature, vol. 370, "PDGF–and insulin–dependent pp70.sup.S6K activation mediated by phosphatidylinositol–3–OH kinase," pp. 71–75 (1994).
Dennis P.B. et al., Mol. & Cell. Biol., vol. 16 (11), "The Principal Rapamycin–Sensitive p70.sup.S6K Phosphorylation Sites, T–229 and T–389, Are Differentially Regulated by Rapamycin–Insensitive Kinase Kinases,".

Downward J., Nature, vol. 376, "A target for PI(3) kinase," pp. 553–554 (1995).
Ferrari, S. et al., Proc. Natl. Acad. Sci. USA, vol. 89, "Activation of p70.sup.S6K is associated with phosphorylation of four clustered sites displaying Ser/Thr–Pro motifs," pp. 7282–7287 (1992).
Ferrari S. et al., J. Biol. Chem., vol. 268 (22), "The Immunosuppressant Rapamycin Induces Inactivation of p70.sup.S6K through Dephosphorylation of a Novel set of Sites," pp. 16091–16094 (1993).
Ferrari and Thomas, Crit. Rev. in Biochem. and Mol. Biol., vol. 29 (6), "S6 Phosphorylation and the p70.sup.S6K ," pp. 385–413 (1994).
Flotow H. & Thomas G., J. Biol. Chem., vol. 267 (5), "Substrate Recognation Determinants of the Mitogen–activated 70K S6 Kinase from Rat Liver," pp. 3074–3078 (1992).
Grove J.R. et al., Molecular and Cell Biology, vol. 11 (11), "Cloning and Expression of Two Human p70 S6 Kinase Polypeptides Differing Only at Their Amino Termini," pp. 5541–5550 (1991).
Hahn C. et al., Proc. Natl. Acad. Sci. USA, vol. 89, "Infectious Sindbis virus transient expression vectors for studying antigen processing and presentation," pp. 2679–2683 (1992).
Harmann B. and Kilimann M.W., FEBS Letters, vol. 273, No. 1,2, "cDNA encoding a 59 kDa homolog of ribosomal protein S6 kinase from rabbit liver," pp. 248–252 (1990).
Ike Y. et al., Nucleic Acids Research, vol. 11 (2), "Solid phase synthesis of polynucleotides. VIII. Synthesis of mixed oligodeoxyribonucleotides by the phosphotriester solid phase method," pp. 477–488 (1983).
Jefferies H.B.J. and Thomas G., "Ribosomal Protein S6 Phosphorylation and Signal Transduction" in Translational Control, J.W.B. Hershey (ed.), Cold Spring Harbor Laboratory Press, Cold Spring Harbor, NY, pp. 389–409 (1996).
Kalderon and Rubin G., Genes & Development, vol. 2, "Isolation and Characterization of Drosophila cAMP–dependent Protein Kinase Genes," p. 1539–1556 (1988).
Kay M.A. & Jacobs–Lorena M., TIG, vol. 3 (12), "Developmental genetics of ribosome synthesis in Drosophila," pp. 347–351 (1987).

(List continued on next page.)

*Primary Examiner*—Gerry Leffers
*Assistant Examiner*—Sumesh Kaushal
(74) *Attorney, Agent, or Firm*—John T. Prince

(57) ABSTRACT

The invention provides *Drosophila melanogaster* p70$^{S6K}$, as well as nucleic acids encoding this kinase. The sequence of *Drosophila* p70$^{S6K}$ and the gene encoding it are represented in SEQ ID No. 2 and 1 respectively. The invention moreover provides mutated forms of *Drosophila* p70$^{S6K}$, including constitutively active and dominant negative forms thereof, which are useful in the study of p70$^{S6K}$ activity. Furthermore, the invention provides expression systems which produce *Drosophila* p70$^{S6K}$ in *Drosophila* and other organisms, and in particular systems in which expression of *Drosophila* p70$^{S6K}$ has been modulated so as to facilitate the study of its activity.

2 Claims, No Drawings

OTHER PUBLICATIONS

Kozma S.C. et al., Proc. Natl. Acad. Sci. USA, vol. 87, "Cloning of the mitogen–activated S6 kinase from rat liver reveals an enzyme of the second messenger subfamily," pp. 7365–7369 (1990).

Lane H.A. et al., EMBO Journal, vol. 11 (5), "Identification and early activation of a Xenopus laevis p70.sup.S6k following progesterone–induced meiotic maturation," pp. 1743–1749 (1992).

Matthias P. et al., Nucleic Acids Research, vol. 17 (15), "Eukaryotic expression vectors for the analysis of mutant proteins," p.6418 (1989).

Mermod J–J. et al., Dev. Biol., vol. 57, "Changes in Rate of RNA Synthesis and Ribosomal Gene Number during Oogenesis of Drosophila melanogaster," pp. 383–402 (1977).

Miller L., Annual Review of Microbiology, vol. 42, "Baculoviruses as Gene Expression Vectors," pp. 177–199 (1988).

Ming X.–F. et al., Nature, vol. 371, "Activation of p70 p85 S6 kinase by a pathway independent of p21 ras," pp. 426–429 (1994).

Mukhopadhyay N.K. et al., J. Biol. Chem., vol. 267 (5), "An Array of Insulin–activated, Proline–directed Serine/Threonine Protein Kinases Phosphorylate the p70 S6 Kinase," pp. 3325–3335 (1992).

Pearson R.B. et al., EMBO Journal, vol. 14 (21), "The principal target of rapamycin–induced p70.sup.S6k inactivation of a novel phosphorylation site within a conserved hydrophobic domain," pp. 5279–5287 (1995).

Pirrotta V., "Cloning Drosophila genes" in Drosophila: a practical approach, D.B. Roberts (ed.), IRL Press, Oxford, UK, pp. 83–110 (1986).

Price D.J. et al., J. Biol. Chem., vol. 266 (25), "Insulin–activated Protein Kinases Phosphorylate a Pseudosubstrate Synthetic Peptide Inhibitor of the p70 S6 Kinase," pp. 16281–16284 (1991).

Richard C. et al., Proc. Natl. Acad. Sci. USA, vol. 89, "A single gene encodes two isoforms of the p70 S6 kinase: Activation upon mitogenic stimulation," pp. 4052–4056 (1992).

Reinhard C. et al., EMBO J., vol. 13 (7), "Nuclear localization of p85.sup.S6k : functional requirement for entry into S phase," pp. 1557–1565 (1994).

Rubin G.M. & Sprading A.C., Nucleic Acids Research, vol. 11 (18), "Vectors for P element–mediated gene transfer in Drosophila," pp. 6341–6351.

Shermoen, A.W. & Kiefer B. I., Cell, vol. 4, "Regulation in rDNA–Deficient Drosophila melanogaster," pp. 275–280 (1975).

Sprading A.C., "The Development of Drosophila melanogaster" in Developmental Genetics of Oogenesis vol. 1, M. Bate & Martinez Arias (ed.), Cold Spring Harbor Laboratory Press, Cold Spring Harbor, NY, pp. 1–70 (1993).

Sprading A.C. et al., Proc. Natl. Acad. Sci. USA, vol. 92, "Gene disruptions using P transposable elements: An integral component of the Drosophila genome project," pp. 10824–10830 (1995).

Stewart M.J. & Denell R., Mol. & Cell. Biol., vol. 13 (4), "Mutations in the Drosophila Gene Encoding Ribosomal Protein S6 Cause Tissue Overgrowth," pp. 2524–2535 (1993).

Stewart M.J. et al., Proc. Natl. Acad. Sci. USA, vol. 93, "The Drosophila p70.sup.Sgk homolog exhibits conserved regulatory elements and rapamycin sensitivity," pp. 10791–10796 (1996).

Stewart M.J. et al., "Identification and Characterization of the Drosphila melanogaster homolog of the p70/p85 S6 Kinase," FASEB Tyrosine Phosphorylation Meeting, Copper Mountain, Colorado, Jul. 1996.

Stewart M.J. et al., "p70 S6 Kinase is Required for Drosphila Development and Oogensis," A. Conf. Dros. Res. 38 1997: 94B. Drosphila Research Conference, Chicago, Illinois, Apr. 1997.

Susa, M. et al., Cell, vol. 57, "EGF Induces Biphasic S6 Kinase Activation: Late Phase is Protein Kinase C–Dependent and Contributes to Mitogenicity,"pp. 817–824 (1989).

Theurkauf W.E. et al., Proc. Natl. Acad. Sci. USA, vol. 83, "Tissue–specific and constitutive .alpha.–tubulin genes of Drosophila melanogaster code for structurally distinct proteins," pp. 8477–8481 (1986).

Thomas G. et al., Exp. Cell. Res., vol. 108, "The Isolation and Analysis of Polysomes and Ribosomal RNA from Cells Growing in Monolayer Culture," pp. 253–258 (1977).

Vaslet C.A. et al., Nature, vol. 285, "Isolation and mapping of a cloned ribosomal protein gene of Drosophila melanogaster," pp. 674–676 (1980).

Vaughn J.L. et al., In Vitro, vol. 13 (4), The Establishment of Two Cell Lines From the Insect Spodoptera Frugiperda (Lepidoptera; Noctuidae), pp. 213–217 (1977).

Watson K. et al., Proc. Natl. Acad. Sci. USA, vol. 93, "A Drosophila gene structurally and functionally homologous to the mammalian 70–kDa S6 kinase gene," pp. 13694–13698 (1996).

Watson K. et al., "Identification of the p70 S6 kinase homologue in D. melanogaster", A Conf. Dros. Res. 37 1996: 365. Dept. of Molecular and Cellular Biology, Harvard University, 16 Divinity Ave., Cambridge, MA.

Weng Q–P. et al., Mol. & Cell. Biol., vol. 15 (5), "Multiple Independent Inputs are Required for Activation of the p70 S6 Kinase," pp. 2333–2340 (1995).

Wieschaus E. & Nusslein–Volhard C., "Looking at embryos" in Drosophila: a practical approach, D.B. Roberts (ed.), IRL Press, Oxford, UK, pp. 199–227 (1986).

Karpen G. & Sprading A., Genetics 132, "Analysis of Subtelometic Heterochromatin in the Drosophila Minichromosome Dp1187 by Single P Element Insertional Mutagenesis," pp. 737–753 (1992).

SEQUENCE LISTING

<160> NUMBER OF SEQ ID NOS: 5

<210> SEQ ID NO 1
<211> LENGTH: 2556
<212> TYPE: DNA
<213> ORGANISM: Drosophila melanogaster

<400> SEQUENCE: 1

```
cgcaaacaaa gaaaaagtg cattttaatt actgattact gcattgcgat taggcgttcg      60
cgaacaacaa cgttttcttg cacatcagcg gactcaaagg gcgcgcgtgg gcagggcatt     120
gagcacagtg tctgtgtgcg tgagtgtggg tgcgttgtgc gtgcgtcgca gtgttggtgc     180
gtgtgccccc atgtgtgtgt gtatttgtat tgccattaac taataaacaa taaccttcgg     240
gccacgacga aagccacgaa atcggcaccg ctgctgttct gttctgtact gttccatctg     300
aaccaaccag ctcaacaaga ggactcatag ccagagacta aaataaaacg ccaacgcgct     360
tccgcccccc ccgcgaaagg agcgcccagt tcaggagcgg accagcggcg atccacttcc     420
catatccata tccaaacaga atcgcactcg cccaaaacac acacgcac gcaatggcgg      480
acgtgagcga tcccagcgaa ctgttcgacc tggagctgca cgacctggaa ctgcaggacg     540
acaaggccag ggactccgac gacgacagga tcgagctgga cgacgttgac ctagaaccgg     600
aattgtgtat taatctgcac caagacactg agggccagga gaccatacag ctctgcgagg     660
agaatgttaa tccaggtaaa atcaagctgg gacccaagga ctttgagctc aagaaggtcc     720
ttggcaaagg cggttatggc aaagtatttc aggtgcgcaa gaccgctgga cgagatgcta     780
acaaatattt tgccatgaag gtgctcaaaa aggcatccat tgtgaccaat caaaaggaca     840
cagcgcacac ccgcgccgag cgcaatatac tcgaggcagt caagcatccc ttcatagtgg     900
agctagttta tgccttccag acagacggaa aactatacct tatacttgaa tatctcagcg     960
gtggagagct gttcatgcat ttggagcgtg agggcatctt cttagaggat accacatgct    1020
tctatctaag cgaaatcatt ttggccttgg gccatctaca caaactgggc atcatctacc    1080
gcgatctgaa gcccgagaac atactgctcg atgcacaggg acatgtgaag ctcacggact    1140
ttggactgtg caaggagcac atacaagagg gtattgtcac ccacaccttc tgcggcacaa    1200
ttgagtacat ggcacctgaa attttgacca gaagtggcca tggcaaagca gtcgactggt    1260
ggtcactggg cgctctcatg tttgacatgc tcacaggagt cccacccttc accgccgaga    1320
atcgcaagaa gaccatcgag accattctga aagccaagct caatctgcca gcctacctca    1380
caccggaagc cagggatctg gtgcgtcgcc tgatgaagcg gcaggaacct cagcgccttg    1440
gcagcggacc cgaggatgcg gcggctgttc aaatacaccc attcttcaaa cacgtcaact    1500
gggacgatgt gctcgccaga cgcctcgagc cgcctataaa accgctcttg agaagcgagg    1560
atgatgtctc acagttcgat acaagattca caagacaaat tccagtggat tcccctgatg    1620
atacaacgct aagcgaaagt gccaatttaa ttttccaagg tttcacctac gttgcaccct    1680
cgatactgga ggatatgcat cgggccaacc ggatgccagc acgctcccca cgacgcactc    1740
cacgccagct gccggacagc agcttccgcc tgcagttccc atcggccaat gtgggcgcca    1800
atgcgcctgc tggccatgca cggtcattcg cagcgatccg ggatgtttgc acgagccacg    1860
ccgccgcatc acatgcagac atttgcgccg cgtccatcgc cggcgcagga cgagatgatg    1920
gacgtgcagg gtctgccgat ggtctaaagg ctggagcgat tgcttcccaa ccaaccaacc    1980
catcccatcc cgtccgttcc gtcgcaaccc agcaactgca tcataagctt cctctcccta    2040
```

-continued

```
cccaaaaaa aaaaaaaaaa aaaaaaaaac agcaaaagat tacagaaatt gacagttact    2100
attatgacgt atgtggagtg tggacttggt taaggatacg gaatgagcag gacgatcatc    2160
aggaggtggc ggaggaggag gaggaggagg aggaggaggc tgagcagcac gaggagcaca    2220
tgacctcagt gcgcgaaatt gttttttgtta agaaaagcg cgctcggatc gcgcttttcg    2280
atgtttatga ttatgagaat gattatgaat atgattatga ttatgaggca gacggagaag    2340
atgattgtgc tacgagaagg aaagcgttcg tttttggata cacctagata ctacagttag    2400
agacatccac ataagcatat gctatagcaa ttactatata catacaccta gagagatggt    2460
tacccgaccc ggatcccaac agccccaaaa acctatccgt gtttatgtat aaagattata    2520
cttacactta tgttttatat aggcaaaaag gttaac                              2556
```

<210> SEQ ID NO 2
<211> LENGTH: 637
<212> TYPE: PRT
<213> ORGANISM: Drosophila melanogaster

<400> SEQUENCE: 2

```
Met Ala Asp Val Ser Asp Pro Ser Glu Leu Phe Asp Leu Glu Leu His
  1               5                  10                  15

Asp Leu Glu Leu Gln Asp Asp Lys Ala Arg Asp Ser Asp Asp Asp Arg
             20                  25                  30

Ile Glu Leu Asp Asp Val Asp Leu Glu Pro Glu Leu Cys Ile Asn Leu
         35                  40                  45

His Gln Asp Thr Glu Gly Gln Glu Thr Ile Gln Leu Cys Glu Glu Asn
     50                  55                  60

Val Asn Pro Gly Lys Ile Lys Leu Gly Pro Lys Asp Phe Glu Leu Lys
 65                  70                  75                  80

Lys Val Leu Gly Lys Gly Gly Tyr Gly Lys Val Phe Gln Val Arg Lys
                 85                  90                  95

Thr Ala Gly Arg Asp Ala Asn Lys Tyr Phe Ala Met Lys Val Leu Lys
            100                 105                 110

Lys Ala Ser Ile Val Thr Asn Gln Lys Asp Thr Ala His Thr Arg Ala
        115                 120                 125

Glu Arg Asn Ile Leu Glu Ala Val Lys His Pro Phe Ile Val Glu Leu
    130                 135                 140

Val Tyr Ala Phe Gln Thr Asp Gly Lys Leu Tyr Leu Ile Leu Glu Tyr
145                 150                 155                 160

Leu Ser Gly Gly Glu Leu Phe Met His Leu Glu Arg Glu Gly Ile Phe
                165                 170                 175

Leu Glu Asp Thr Thr Cys Phe Tyr Leu Ser Glu Ile Ile Leu Ala Leu
            180                 185                 190

Gly His Leu His Lys Leu Gly Ile Ile Tyr Arg Asp Leu Lys Pro Glu
        195                 200                 205

Asn Ile Leu Leu Asp Ala Gln Gly His Val Lys Leu Thr Asp Phe Gly
    210                 215                 220

Leu Cys Lys Glu His Ile Gln Glu Gly Ile Val Thr His Thr Phe Cys
225                 230                 235                 240

Gly Thr Ile Glu Tyr Met Ala Pro Glu Ile Leu Thr Arg Ser Gly His
                245                 250                 255

Gly Lys Ala Val Asp Trp Trp Ser Leu Gly Ala Leu Met Phe Asp Met
            260                 265                 270

Leu Thr Gly Val Pro Pro Phe Thr Ala Glu Asn Arg Lys Lys Thr Ile
```

-continued

```
                    275                 280                 285
Glu Thr Ile Leu Lys Ala Lys Leu Asn Leu Pro Ala Tyr Leu Thr Pro
        290                 295                 300
Glu Ala Arg Asp Leu Val Arg Arg Leu Met Lys Arg Gln Glu Pro Gln
305                 310                 315                 320
Arg Leu Gly Ser Gly Pro Glu Asp Ala Ala Val Gln Ile His Pro
            325                 330                 335
Phe Phe Lys His Val Asn Trp Asp Val Leu Ala Arg Arg Leu Glu
                340                 345                 350
Pro Pro Ile Lys Pro Leu Leu Arg Ser Glu Asp Val Ser Gln Phe
            355                 360                 365
Asp Thr Arg Phe Thr Arg Gln Ile Pro Val Asp Ser Pro Asp Thr
    370                 375                 380
Thr Leu Ser Glu Ser Ala Asn Leu Ile Phe Gln Gly Phe Thr Tyr Val
385                 390                 395                 400
Ala Pro Ser Ile Leu Glu Asp Met His Arg Ala Asn Arg Met Pro Ala
                405                 410                 415
Arg Ser Pro Arg Arg Thr Pro Arg Gln Leu Pro Asp Ser Ser Phe Arg
            420                 425                 430
Leu Gln Phe Pro Ser Ala Asn Val Gly Ala Asn Ala Pro Ala Gly His
                435                 440                 445
Ala Arg Ser Phe Ala Ala Ile Arg Asp Val Cys Thr Ser His Ala Ala
    450                 455                 460
Ala Ser His Ala Asp Ile Cys Ala Ala Ser Ile Ala Gly Ala Gly Arg
465                 470                 475                 480
Asp Asp Gly Arg Ala Gly Ser Ala Asp Gly Leu Lys Ala Gly Ala Ile
                485                 490                 495
Ala Ser Gln Pro Thr Asn Pro Ser His Pro Val Arg Ser Val Ala Thr
            500                 505                 510
Gln Gln Leu His His Lys Leu Pro Leu Pro Thr Pro Lys Lys Lys
            515                 520                 525
Lys Lys Lys Lys Gln Gln Lys Ile Thr Glu Ile Asp Ser Tyr Tyr Tyr
530                 535                 540
Asp Val Cys Gly Val Trp Thr Trp Leu Arg Ile Arg Asn Glu Gln Asp
545                 550                 555                 560
Asp His Gln Glu Val Ala Glu Glu Glu Glu Glu Glu Glu Glu Ala
                565                 570                 575
Glu Gln His Glu Glu His Met Thr Ser Val Arg Glu Ile Val Phe Val
            580                 585                 590
Lys Glu Lys Arg Ala Arg Ile Ala Leu Phe Asp Val Tyr Asp Tyr Glu
            595                 600                 605
Asn Asp Tyr Glu Tyr Asp Tyr Asp Tyr Glu Ala Asp Gly Glu Asp Asp
    610                 615                 620
Cys Ala Thr Arg Arg Lys Ala Phe Val Phe Gly Tyr Thr
625                 630                 635
```

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence:designed peptide based on N-terminus of SEQ ID NO:2

<400> SEQUENCE: 3

-continued

```
Met Ala Asp Val Ser Asp Pro Ser Glu Leu Phe Asp Leu Glu Leu His
  1               5                  10                  15

Asp Leu Glu Tyr
             20

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:peptide
      fragment of SEQ ID NO:2

<400> SEQUENCE: 4

Arg Ser Pro Arg Arg Thr Pro Arg
  1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence:mammalian
      autoinhibitory domain

<400> SEQUENCE: 5

Arg Ser Pro Arg Arg Phe Ile Asp Ser Pro Arg
  1               5                  10
```

DROSOPHILA MELANOGASTER P70 S6 KINASE

This application is a div of 09/817,310 filed Mar. 26, 2001 now U.S. Pat. No. 6,534,311, which is a con of 09/230,247 filed Apr. 16, 1999 which is a 371 of PCT/EP97/03680 filed Jul. 11, 1992 now abandoned.

The present invention relates to a protein kinase enzyme, specifically to p70 S6 kinase ($p70^{S6K}$) isolated from *Drosophila melanogaster*.

In the signal transduction pathway mediating the multiple phosphorylation of 40S ribosomal protein S6 in response to mitogens and oncogenes, the most proximal signalling components to S6 are $p70^{S6K}$ and $p85^{S6K}$ (Ferrari, S. & Thomas, G. (1994) CRC Crit. Rev. Biochem. Mol. Biol. 29, 385–413; Jefferies, H. B. J. & Thomas, G. (1995) in Translational Control, eds. Hershey, J. W. B., Mathews, M. B. & Sonenberg, N., Cold Spring Harbor Press, Cold Spring Harbor). Both of these kinase isoforms are generated from a common mRNA transcript through the use of alternative initiation translation start sites, residing within 23 codons of one another. The additional 23 amino acid extension at the amino terminus of $p85^{S6K}$ contains a nuclear localisation sequence, which constitutively targets this isoform to the nucleus, whereas $p70^{S6K}$ appears to be exclusively cytoplasmic. Consistent with the localisation of S6 in both compartments of the cell, the available data suggest that both kinase isoforms are regulated in a closely coordinated fashion. Little is known regarding the functional role of $p85^{S6K}$ and phosphorylated S6 in the nucleus, however recent studies employing the immunosuppressant rapamycin have led to the hypothesis that $p70^{S6K}$, through increased S6 phosphorylation, is involved in the selective translational upregulation of a family of mRNAs characterised by a oligopyrimidine tract at their 5' transcriptional start sites. Although these mRNAs, termed 5' TOP, comprise a small family, they can represent up to 20–30% of the cells mRNA transcripts, and in most cases code for essential gene products of the translational apparatus, such as ribosomal proteins.

The link between mitogen-induced $p70^{S6K}$ activation and the translational upregulation of 5' TOP mRNAs is based on the selective effects of the rapamycin-FKBP12 gain-of-function inhibitory complex on both responses. Activation of $p70^{S6K}$ is associated with the phosphorylation of the enzyme at multiple residues, which exhibit two distinct phosphorylation motifs. The sites initially identified are flanked by a proline in the +1 position (Ferrari, S., et al. (1992) Proc. Nat i. Acad. Sci. USA 89, 7282–7285) and, with the exception of S411, are rapamycin resistant. The second set of sites is flanked in the +1 and −1 positions by large aromatic residues, and exhibit rapamycin sensitivity (Pearson, R. B., et al. (1995) EMBO J. 14, 5279–5287). Of these latter sites the principal target of rapamycin-induced $p70^{S6K}$ inactivation and dephosphorylation is T389 in the linker region, that couples the catalytic and autoinhibitory domains. Conversion of this site to an acidic residue confers rapamycin resistance and constitutive activity on the kinase. Truncation mutants of $p70^{S6K}$ have revealed, that in the absence of the amino-terminus, rapamycin can no longer block mitogen-induced T389 phosphorylation or kinase activation, demonstrating that inhibitory effects of rapamycin are not exerted through blocking the activation of an upstream kinase. However the mechanism by which rapamycin affects $p70^{S6K}$ activation through the amino-terminus remains unresolved. The failure to identify the immediate upstream $p70^{S6K}$ kinases as well as the mechanism by which rapamycin regulates $p70^{S6K}$ activation is largely explained by the multiple events required to bring about this response and the failure to reconstitute these events in vitro. This failure prompted the application of a number of complementary indirect approaches, including the use of inhibitors (Chung, J., et al. (1994) Nature 370, 71–75), dominant negative signalling molecules (Ming, X. F., et al. (1994) Nature 371, 426–429), and growth factor receptor mutants in the search for upstream components that regulate this response. However, as yet, this strategy has not yielded any additional insight into the identity of the upstream $p70^{S6K}$ kinases nor the mechanism for the selective effects of rapamycin on the kinase.

A powerful system which could complement the phosphorylation site studies described above, as well as resolve conflicting issues concerning the involvement of specific signalling molecules, is the use of developmental genetics. The use of genetic systems has proven extremely important in establishing the components that make up specific signal transduction pathways. For example, the application of a genetic approach to the study of the *Drosophila* sevenless mutant played a direct role in elucidating the signalling components of the MAP kinase pathway. In the case of $p70^{S6K}$, this system offers the additional attraction that in *Drosophila*, unlike yeast and slime moulds, the majority of ribosomal proteins contain a 5'TOP and their expression is selectively regulated at the translational level, in a manner similar to that found in mammals. Thus, the identification of a *Drosophila* $p70^{S6K}$ homologue could prove very important in identifying immediate upstream kinases and downstream targets as well as the mechanism by which rapamycin influences these responses.

SUMMARY OF THE INVENTION

The invention accordingly provides *Drosophila melanogaster* $p70^{S6K}$, as well as nucleic acids encoding this kinase. The sequence of *Drosophila* $p70^{S6K}$ and the gene encoding it are represented in SEQ ID No. 2 and 1 respectively. The invention moreover provides mutated forms of *Drosophila* $p70^{S6K}$, including constitutively active and dominant negative forms thereof, which are useful in the study of $p70^{S6K}$ activity. Furthermore, the invention provides expression systems which produce *Drosophila* $p70^{S6K}$ in *Drosophila* and other organisms, and in particular systems in which expression of *Drosophila* $p70^{S6K}$ has been modulated so as to facilitate the study of its activity.

DETAILED DESCRIPTION OF THE INVENTION

Polypeptides according to the invention include *Drosophila* $p70^{S6K}$ and derivatives thereof which retain at least one common structural determinant of *Drosophila* $p70^{S6K}$.

"Common structural determinant" means that the derivative in question possesses at least one structural feature of *Drosophila* $p70^{S6K}$. Structural features includes possession of an epitope or antigenic site that is capable of cross-reacting with antibodies raised against a naturally occurring or denatured *Drosophila* $p70^{S6K}$ polypeptide or fragment thereof, possession of amino acid sequence identity with *Drosophila* $p70^{S6K}$ and features having a common structure/function relationship. Thus *Drosophila* $p70^{S6K}$ as provided by the present invention includes splice variants encoded by mRNA generated by alternative splicing of a primary transcript, amino acid mutants, glycosylation variants and other covalent derivatives of *Drosophila* $p70^{S6K}$ which retain the physiological and/or physical properties of *Droso-* phila p70$^{S6K}$. Exemplary derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope. Further included are naturally occurring variants of Drosophila p70$^{S6K}$ found within a particular species. Such a variant may be encoded by a related gene of the same gene family, by an allelic variant of a particular gene, or represent an alternative splicing variant of the Drosophila p70$^{S6K}$ gene.

Derivatives which retain common structural features can be fragments of Drosophila p70$^{S6K}$. Fragments of Drosophila p70$^{S6K}$ comprise individual domains thereof, as well as smaller polypeptides derived from the domains. Preferably, smaller polypeptides derived from Drosophila p70$^{S6K}$ according to the invention define a single feature which is characteristic of Drosophila p70$^{S6K}$. Fragments may in theory be almost any size, as long as they retain one feature of Drosophila p70$^{S6K}$. Preferably, fragments will be between 5 and 350 amino acids in length. Longer fragments are regarded as truncations of the full-length Drosophila p70$^{S6K}$ and generally encompassed by the term "Drosophila p70$^{S6K}$".

Derivatives of Drosophila p70$^{S6K}$ also comprise mutants thereof, which may contain amino acid deletions, additions or substitutions, subject to the requirement to maintain at least one feature characteristic of Drosophila p70$^{S6K}$. Thus, conservative amino acid substitutions may be made substantially without altering the nature of Drosophila p70$^{S6K}$, as may truncations from the 5' or 3' ends. Deletions and substitutions may moreover be made to the fragments of Drosophila p70$^{S6K}$ comprised in the invention. Drosophila p70$^{S6K}$ mutants may be produced from a DNA encoding Drosophila p70$^{S6K}$ which has been subjected to in vitro mutagenesis, for example resulting in an addition, exchange and/or deletion of one or more amino acids. For example, substitutional, deletional or insertional variants of Drosophila p70$^{S6K}$ can be prepared by recombinant methods and screened for immuno-crossreactivity with the native forms of Drosophila p70$^{S6K}$.

The invention particularly comprises mutants of Drosophila p70$^{S6K}$ in which activity has been enhanced or reduced by amino acid substitution. Generally, the preferred substitutions are made at the residues homologous to those which have previously been indicated to be important in mouse p70$^{S6K}$. In the case of a "homologous" amino acid residue, it is intended to indicate that the homologous amino acids are present in a similar positional context and perform a similar role in different mouse and Drosophila enzymes. Thus, $T_{389}$, $T_{229}$ and $S_{371}$ in mouse p70$^{S6K}$ are homologous to $T_{389}$, $T_{238}$ and $S_{380}$ in Drosophila p70$^{S6K}$. $T_{389}$ is particularly indicated for mutation to an acidic amino acid residue in order to produce a constitutively active kinase.

Preferably, the $T_{389}$ mutation is combined with one or more additional serine or threonine substitutions involving insertion of an acidic amino acid in place thereof. For example, combination of the $T_{389} \rightarrow E$ with one or more of the $D_3E$ mutations is particularly advantageous.

The $D_3E$ mutations as herein defined comprises the mutations previously described in mammalian p70$^{S6K}$ by Ferrari et al., (1993) J. Biol. Chem. 268, 16091–16094, and equivalent mutations in Drosophila kinase. These mutations consist in the conversion of homologues of $S_{411}$, $S_{418}$ and $S_{424}$ to D and the conversion of the homologue of $T_{421}$ to E. The combination of any one or more of these mutations with the $T_{389} \rightarrow E$ mutation further increases the basal activity of p70$^{S6K}$ and imparts rapamycin resistance thereto. Preferably, the $T_{389} \rightarrow E$ mutation is combined with all of the $D_3E$ mutations.

Moreover, mutations may be effected at sites homologous to $S_{404}$ on p70$^{S6K}$. In general, threonine residues are converted to glutamic acid and serine residues are converted to aspartic acid.

Interestingly, although $T_{389}$ is the major rapamycin-sensitive site involved in the regulation of p70$^{S6K}$, it is not the only site involved in p70$^{S6K}$ activation. A second site which must be phosphorylated for p70$^{S6K}$ activation is $T_{229}$ ($T_{238}$). Dephosphorylation of this site results in immediate loss of any kinase activity. Moreover, mutation of this site to an acidic amino acid results in irreversible loss of kinase activity. Phosphorylation of $T_{229}$ is itself dependent on phosphorylation of $T_{389}$. Thus, a regulatory p70$^{S6K}$ kinase acts on $T_{389}$, phosphorylation of this site being responsible for activation of a further p70$^{S6K}$ kinase which phosphorylates $T_{229}$.

The invention accordingly provides Drosophila p70$^{S6K}$ comprising the $D_3E$ and $T_{389} \rightarrow E$ homologous mutations. Such a kinase enzyme is useful as a tool for identifying p70$^{S6K}$ kinases responsible for both regulation of the p70$^{S6K}$ related kinase and direct activation thereof through $T_{229}$.

Moreover, the invention provides Drosophila p70$^{S6K}$ comprising a $T_{229} \rightarrow A$ and/or a $K100 \rightarrow E$ homologous mutation. These mutants are dominant negative mutants of p70$^{S6K}$, irreversibly inactive and capable of preventing activation of endogenous p70$^{S6K}$ in a cell by competing therewith for factors essential for p70$^{S6K}$ activation. The K100 residue lies in the ATP binding site of p70$^{S6K}$. The dominant negative mutants compete for the upstream kinase kinase enzyme responsible for p70$^{S6K}$ activation and prevent its becoming available to phosphorylate endogenous p70$^{S6K}$ and other downstream targets. The mutants are useful as tools for defining the p70$^{S6K}$ signalling pathway, and as agents for blocking the upstream kinase kinase.

The fragments, mutants and other derivatives of Drosophila p70$^{S6K}$ preferably retain substantial homology with Drosophila p70$^{S6K}$. As used herein, "homology" means that the two entities share sufficient characteristics for the skilled person to determine that they are similar in origin and function. Preferably, homology is used to refer to sequence identity. Thus, the derivatives of Drosophila p70$^{S6K}$ preferably retain substantial sequence identity with the sequence of SEQ ID No. 2.

"Substantial homology", where homology indicates sequence identity, means more than 65% sequence identity, preferably more than 75% sequence identity and most preferably a sequence identity of 90% or more.

In still another aspect of the invention, the nucleic acid is DNA and further comprises a replicable vector comprising the nucleic acid encoding Drosophila p70$^{S6K}$ operably linked to control sequences recognised by a host transformed by the vector. Furthermore the invention provides host cells transformed with such a vector and a method of using a nucleic acid encoding Drosophila p70$^{S6K}$ to effect the production of Drosophila p70$^{S6K}$, comprising expressing Drosophila p70$^{S6K}$ nucleic acid in a culture of the transformed host cells and, if desired, recovering Drosophila p70$^{S6K}$ from the host cell culture.

Additionally, the present invention relates to isolated Drosophila p70$^{S6K}$ proteins and derivatives thereof encoded by the above-described nucleic acids.

In accordance with the present invention, there are provided isolated nucleic acids encoding Drosophila p70$^{S6K}$, or fragments thereof. In particular, the invention provides a DNA molecule encoding *Drosophila* p70$^{S6K}$, or a fragment thereof. By definition, such a DNA comprises a coding single stranded DNA, a double stranded DNA of said coding DNA and complementary DNA thereto, or this complementary (single stranded) DNA itself. An exemplary nucleic acid encoding *Drosophila* p70$^{S6K}$ is represented in SEQ ID No. 1.

Isolated *Drosophila* p70$^{S6K}$ nucleic acid includes nucleic acid that is free from at least one contaminant nucleic acid with which it is ordinarily associated in the natural source of *Drosophila* p70$^{S6K}$ nucleic acid or in crude nucleic acid preparations, such as DNA libraries and the like. Isolated nucleic acid thus is present in other than in the form or setting in which it is found in nature. However, isolated *Drosophila* p70$^{S6K}$ encoding nucleic acid includes *Drosophila* p70$^{S6K}$ nucleic acid in ordinarily *Drosophila* p70$^{S6K}$-expressing cells where the nucleic acid is in a chromosomal location different from that of natural cells or is otherwise flanked by a different DNA sequence than that found in nature.

The preferred sequence encoding *Drosophila* p70$^{S6K}$ is that having substantially the same nucleotide sequence as the coding sequences in SEQ ID No. 1, with the nucleic acid having the same sequence as the coding sequence in SEQ ID No. 1 being most preferred. As used herein, nucleotide sequences which are substantially the same share at least about 90% identity. However, in the case of splice variants having e.g. an additional exon sequence homology may be lower.

The nucleic acids of the invention, whether used as probes or otherwise, are preferably substantially homologous to the sequence of *Drosophila* p70$^{S6K}$ as shown in SEQ ID No. 1. The terms "substantially" and "homologous" are used as hereinbefore defined with reference to the *Drosophila* p70$^{S6K}$ polypeptide.

Preferably, nucleic acids according to the invention are fragments of the *Drosophila* p70$^{S6K}$-encoding sequence, or derivatives thereof as hereinbefore defined in relation to polypeptides. Fragments of the nucleic acid sequence of a few nucleotides in length, preferably 5 to 150 nucleotides in length, are especially useful as probes.

Exemplary nucleic acids can alternatively be characterised as those nucleotide sequences which encode a *Drosophila* p70$^{S6K}$ protein and hybridise to the DNA sequences set forth SEQ ID No. 1, or a selected fragment of said DNA sequence. Preferred are such sequences encoding *Drosophila* p70$^{S6K}$ which hybridise under high-stringency conditions to the sequence of SEQ ID No. 1.

Stringency of hybridisation refers to conditions under which polynucleic acids hybrids are stable. Such conditions are evident to those of ordinary skill in the field. As known to those of skill in the art, the stability of hybrids is reflected in the melting temperature ($T_m$) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na$^+$ at 65–68° C. High stringency conditions can be provided, for example, by hybridisation in an aqueous solution containing 6× SSC, 5× Denhardt's, 1% SDS (sodium dodecyl sulphate), 0.1 M sodium pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1× SSC, 0.1% SDS.

Moderate stringency refers to conditions equivalent to hybridisation in the above described solution but at about 60–62° C. In that case the final wash is performed at the hybridisation temperature in 1× SSC, 0.1% SDS.

Low stringency refers to conditions equivalent to hybridisation in the above described solution at about 50–52° C. In that case, the final wash is performed at the hybridisation temperature in 2× SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Given the guidance provided herein, the nucleic acids of the invention are obtainable according to methods well known in the art. For example, a DNA of the invention is obtainable by chemical synthesis, using polymerase chain reaction (PCR) or by screening a genomic library or a suitable cDNA library prepared from a source believed to possess *Drosophila* p70$^{S6K}$ and to express it at a detectable level.

Chemical methods for synthesis of a nucleic acid of interest are known in the art and include triester, phosphite, phosphoramidite and H-phosphonate methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

An alternative means to isolate the gene encoding *Drosophila* p70$^{S6K}$ is to use PCR technology, for example as described in section 14 of Sambrook et al., 1989. This method requires the use of oligonucleotide probes that will hybridise to *Drosophila* p70$^{S6K}$ nucleic acid. Strategies for selection of oligonucleotides are described below.

Libraries are screened with probes or analytical tools designed to identify the gene of interest or the protein encoded by it. For cDNA expression libraries suitable means include monoclonal or polyclonal antibodies that recognise and specifically bind to *Drosophila* p70$^{S6K}$; oligonucleotides of about 20 to 80 bases in length that encode *Drosophila* p70$^{S6K}$ cDNA; and/or complementary or homologous cDNAs or fragments thereof that encode the same or a hybridising gene. Appropriate probes for screening genomic DNA libraries include, but are not limited to oligonucleotides, cDNAs or fragments thereof that encode the same or hybridising DNA; and/or homologous genomic DNAs or fragments thereof.

A nucleic acid encoding *Drosophila* p70$^{S6K}$ may be isolated by screening suitable cDNA or genomic libraries under suitable hybridisation conditions with a probe, i.e. a nucleic acid disclosed herein including oligonucleotides derivable from the sequences set forth in SEQ ID NO. 1.

Suitable libraries can be prepared from *Drosophila* by standard methodology.

As used herein, a probe is e.g. a single-stranded DNA or RNA that has a sequence of nucleotides that includes between 10 and 50, preferably between 15 and 30 and most preferably at least about 20 contiguous bases that are the same as (or the complement of) an equivalent or greater number of contiguous bases set forth in SEQ ID No. 1. The nucleic acid sequences selected as probes should be of sufficient length and sufficiently unambiguous so that false positive results are minimised. The nucleotide sequences are usually based on conserved or highly homologous nucleotide sequences or regions of *Drosophila* p70$^{S6K}$. The nucleic acids used as probes may be degenerate at one or more positions. The use of degenerate oligonucleotides may be of particular importance where a library is screened from a species in which preferential codon usage in that species is not known.

Preferred regions from which to construct probes include 5' and/or 3' coding sequences, sequences predicted to encode ligand binding sites, such as the catalytically active site, and the like. For example, either the full-length cDNA clone disclosed herein or fragments thereof can be used as probes. Preferably, nucleic acid probes of the invention are labelled with suitable label means for ready detection upon hybridisation. For example, a suitable label means is a radiolabel. The preferred method of labelling a DNA fragment is by incorporating $\alpha^{32P}$ dATP with the Klenow fragment of DNA polymerase in a random priming reaction, as is well known in the art. Oligonucleotides are usually end-labelled with $\gamma^{32P}$-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

After screening the library, e.g. with a portion of DNA including substantially the entire *Drosophila* p70$^{S6K}$-encoding sequence or a suitable oligonucleotide based on a portion of said DNA, positive clones are identified by detecting a hybridisation signal; the identified clones are characterised by restriction enzyme mapping and/or DNA sequence analysis, and then examined, e.g. by comparison with the sequences set forth herein, to ascertain whether they include DNA encoding a complete *Drosophila* p70$^{S6K}$ (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNAs and deduced amino acid sequences provided herein.

In order to detect any abnormality of endogenous *Drosophila* p70$^{S6K}$, genetic screening may be carried out using the nucleotide sequences of the invention as hybridisation probes. Also, based on the nucleic acid sequences provided herein antisense-type therapeutic agents may be designed.

It is envisaged that the nucleic acid of the invention can be readily modified by nucleotide substitution, nucleotide deletion, nucleotide insertion or inversion of a nucleotide stretch, and any combination thereof. Such mutants can be used e.g. to produce a *Drosophila* p70$^{S6K}$ mutant that has an amino acid sequence differing from the *Drosophila* p70$^{S6K}$ sequences as found in nature. Mutagenesis may be predetermined (site-specific) or random. A mutation which is not a silent mutation must not place sequences out of reading frames and preferably will not create complementary regions that could hybridise to produce secondary mRNA structure such as loops or hairpins.

If required, nucleic acids encoding *Drosophila* p70$^{S6K}$-related enzymes may be cloned from *Drosophila* spp. according to established procedures using probes derived from *Drosophila* p70$^{S6K}$ itself or any of the published sequences of related D-ala-D-ala ligases. In particular, such DNAs can be prepared by:

a) isolating mRNA from suitable *Drosophila* cells, selecting the desired mRNA, for example by hybridisation with a DNA probe or by expression in a suitable expression system and screening for expression of the desired polypeptide, preparing single-stranded cDNA complementary to that mRNA, then double-stranded cDNA therefrom, or
  b) isolating cDNA from a cDNA library and selecting the desired cDNA, for example using a DNA probe or using a suitable expression system and screening for expression of the desired polypeptide,
  c) incorporating the double-stranded DNA of step a) or b) into an appropriate expression vector,
  d) transforming appropriate host cells with the vector and isolating the desired DNA.

Messenger RNA (step a) is isolated by known methods. Isolation methods involve, for example, homogenizing cells in the presence of a detergent and a ribonuclease inhibitor, for example heparin, guanidinium isothiocyanate or mercaptoethanol, extracting the mRNA with a chloroform-phenol mixture, optionally in the presence of salt and buffer solutions, detergents and/or cation chelating agents, and precipitating mRNA from the remaining aqueous, salt-containing phase with ethanol, isopropanol or the like. The isolated mRNA may be further purified by centrifuging in a caesium chloride gradient followed by ethanol precipitation and/or by chromatographic methods, for example affinity chromatography, for example chromatography on oligo(dT) cellulose or on oligo(U) sepharose if it is polyadenylated. Preferably, such purified total mRNA is fractionated according to size by gradient centrifugation, for example in a linear sucrose gradient, or chromatography on suitable size fractionation columns, for example on agarose gels.

The desired mRNA is selected by screening the mRNA directly with a DNA probe, or by translation in suitable cells or cell-free systems and screening the obtained polypeptides.

The selection of the desired mRNA is preferably achieved using a DNA hybridisation probe, thereby avoiding the additional step of translation. Suitable DNA probes are DNAs of known nucleotide sequence consisting of at least 17 nucleotides derived from DNAs encoding *Drosophila* p70$^{S6K}$ or a related ligase.

Synthetic DNA probes are synthesised according to known methods as detailed hereinbelow, preferably by stepwise condensation using the solid phase phosphotriester, phosphite triester or phosphoramidite method, for example the condensation of dinucleotide coupling units by the phosphotriester method. These methods are adapted to the synthesis of mixtures of the desired oligonucleotides by using mixtures of two, three or four nucleotides dA, dC, dG and/or dT in protected form or the corresponding dinucleotide coupling units in the appropriate condensation step as described by Y. Ike et al. (Nucleic Acids Research 11, 477, 1983).

For hybridisation, the DNA probes are labelled, for example radioactively labelled by the well known kinase reaction. The hybridisation of the size-fractionated mRNA with the DNA probes containing a label is performed according to known procedures, i.e. in buffer and salt solutions containing adjuncts, for example calcium chelators, viscosity regulating compounds, proteins, irrelevant DNA and the like, at temperatures favouring selective hybridisation, for example between 0° C. and 80° C., for example between 25° C. and 50° C. or around 65° C., preferably at around 20° lower than the hybrid double-stranded DNA melting temperature.

Fractionated mRNA may be translated in cells, for example frog oocytes, or in cell-free systems, for example in reticulocyte lysates or wheat germ extracts. The obtained polypeptides are screened for D-ala-D-ala ligase activity or for reaction with antibodies raised against the Drosophila $p70^{S6K}$ related ligase, for example in an immunoassay, for example radioimmunoassay, enzyme immunoassay or immunoassay with fluorescent markers. Such immunoassays and the preparation of polyclonal and monoclonal antibodies are well known in the art and are applied accordingly.

The preparation of a single-stranded complementary DNA (CDNA) from the selected mRNA template is well known in the art, as is the preparation of a double-stranded DNA from a single-stranded DNA. The mRNA template is incubated with a mixture of deoxynucleoside triphosphates, optionally radioactively labelled deoxynucleoside triphosphates (in order to be able to screen the result of the reaction), a primer sequence such as an oligo-dT residue hybridising with the poly(A) tail of the mRNA and a suitable enzyme such as a reverse transcriptase for example from avian myeloblastosis virus (AMV). After degradation of the template mRNA for example by alkaline hydrolysis, the cDNA is incubated with a mixture of deoxynucleoside triphosphates and a suitable enzyme to give a double-stranded DNA. Suitable enzymes are for instance a reverse transcriptase, the Klenow fragment of E. coli DNA polymerase I or T4 DNA polymerase. Usually, a hairpin loop structure formed spontaneously by the single-stranded cDNA acts as a primer for the synthesis of the second strand. This hairpin structure is removed by digestion with S1 nuclease. Alternatively, the 3'-end of the single-stranded DNA is first extended by homopolymeric deoxynucleotide tails prior to the hydrolysis of the mRNA template and the subsequent synthesis of the second cDNA strand.

In the alternative, double-stranded cDNA is isolated from a cDNA library and screened for the desired cDNA (step b). The cDNA library is constructed by isolating mRNA from Drosophila cells, and preparing single-stranded and double-stranded cDNA therefrom as described above. This cDNA is digested with suitable restriction endonucleases and incorporated into λ phage, for example k charon 4A or λ gt11 following established procedures. The cDNA library replicated on nitrocellulose membranes is screened by using a DNA probe as described hereinbefore, or expressed in a suitable expression system and the obtained polypeptides screened for reaction with an antibody specific for Drosophila $p70^{S6K}$.

A variety of methods are known in the art for the incorporation of double-stranded cDNA into an appropriate vector (step c). For example, complementary homopolymer tracts may be added to the double-stranded DNA and the vector DNA by incubation in the presence of the corresponding deoxynucleoside triphosphates and an enzyme such as terminal deoxynucleotidyl transferase. The vector and double-stranded DNA are then joined by base pairing between the complementary homopolymeric tails and finally ligated by specific joining enzymes such as ligases. Other possibilities are the addition of synthetic linkers to the termini of the double-stranded DNA, or the incorporation of the double-stranded DNA into the vector by blunt- or staggered-end ligation.

The transformation of appropriate host cells with the obtained hybrid vector (step d) and the selection of transformed host cells (step e) are well known in the art. Hybrid vectors and host cells may be particularly suitable for the production of DNA, or for the production of the desired Drosophila $p70^{S6K}$.

The isolation of the desired DNA is achieved by methods known in the art, for example extraction with phenol and/or chloroform or on glass beads. Optionally, the DNA can be further manipulated for example by treatment with mutagenic agents to obtain mutants, or by digestion with restriction enzymes to obtain fragments, modify one or both termini to facilitate incorporation into the vector.

The cDNA or genomic DNA encoding native or mutant Drosophila $p70^{S6K}$ can be incorporated into vectors for further manipulation. As used herein, vector (or plasmid) refers to discrete elements that are used to introduce heterologous DNA into cells for either expression or replication thereof. Selection and use of such vehicles are well within the skill of the artisan. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2μ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another organism for expression. For example, a vector is cloned in E. coli and then the same vector is transfected into yeast or mammalian cells even though it is not capable of replicating independently of the host cell chromosome. DNA may also be replicated by insertion into the host genome. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript® vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells competent to take up *Drosophila* $p70^{S6K}$ nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes *Drosophila* $p70^{S6K}$. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

An expression vector includes any vector capable of expressing *Drosophila* $p70^{S6K}$ nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding *Drosophila* $p70^{S6K}$ may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding *Drosophila* $p70^{S6K}$ in mammalian cells. Transient expression usually involves the use of an expression vector that is able to replicate efficiently in a host cell, such that the host cell accumulates many copies of the expression vector, and, in turn, synthesises high levels of *Drosophila* $p70^{S6K}$. For the purposes of the present invention, transient expression systems are useful e.g. for identifying *Drosophila* $p70^{S6K}$ mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing *Drosophila* $p70^{S6K}$ expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe based on a sequence provided herein. Those skilled in the art will readily envisage how these methods may be modified, if desired.

Expression and cloning vectors usually contain a promoter that is recognised by the host organism and is operably linked to *Drosophila* $p70^{S6K}$ nucleic acid. Such a promoter may be inducible or constitutive. The promoters are operably linked to DNA encoding *Drosophila* $p70^{S6K}$ by removing the promoter from the source DNA by restriction enzyme digestion and inserting the isolated promoter sequence into the vector. Both the native *Drosophila* $p70^{S6K}$ promoter sequence and many heterologous promoters may be used to direct amplification and/or expression of *Drosophila* $p70^{S6K}$ DNA.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding *Drosophila* $p70^{S6K}$, using linkers or adaptors to supply any required restriction sites. Promoters for use in bacterial systems will also generally contain a Shine-Delgarno sequence operably linked to the DNA encoding *Drosophila* $p70^{S6K}$.

Moreover, the *Drosophila* $p70^{S6K}$ gene according to the invention preferably includes a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the α- or a-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, or a promoter from the TATA binding protein (TBP) gene can be used.

Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

Drosophila $p70^{S6K}$ gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with Drosophila $p70^{S6K}$ sequence, provided such promoters are compatible with the host cell systems.

Transcription of a DNA encoding Drosophila $p70^{S6K}$ by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to Drosophila $p70^{S6K}$DNA, but is preferably located at a site 5' from the promoter.

Suitable eukaryotic host cells for expression of Drosophila $p70^{S6K}$ include yeast, fungi, insect, plant, animal, human, or nucleated cells from other multicellular organisms will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding Drosophila $p70^{S6K}$.

In addition to being useful for the production of recombinant Drosophila $p70^{S6K}$ protein, these nucleic acids are also useful as probes, thus readily enabling those skilled in the art to identify and/or isolate nucleic acid encoding Drosophila $p70^{S6K}$ or related enzymes from other Drosophila spp. The nucleic acid may be unlabelled or labelled with a detectable moiety. Furthermore, nucleic acid according to the invention is useful e.g. in a method determining the presence of Drosophila $p70^{S6K}$-specific nucleic acid, said method comprising hybridising the DNA (or RNA) encoding (or complementary to) Drosophila $p70^{S6K}$ to test sample nucleic acid and determining the presence of Drosophila $p70^{S6K}$. In another aspect, the invention provides nucleic acid sequence that is complementary to, or hybridises under stringent conditions to, a nucleic acid sequence encoding Drosophila $70^{S6K}$.

The invention also provides a method for amplifying a nucleic acid test sample comprising priming a nucleic acid polymerase (chain) reaction with nucleic acid (DNA or RNA) encoding (or complementary to) Drosophila $p70^{S6K}$.

In accordance with another embodiment of the present invention, there are provided cells containing the above-described nucleic acids. Such host cells such as prokaryote, yeast and higher eukaryote cells may be used for replicating DNA and producing Drosophila $p70^{S6K}$. Suitable prokaryotes include eubacteria, such as Gram-negative or Gram-positive organisms, such as E. coli, e.g. E. coli K-12 strains, DH5α and HB101, or Bacilli, such as B. subtilis. Further hosts suitable for Drosophila $p70^{S6K}$ encoding vectors include eukaryotic microbes such as filamentous fungi or yeast, e.g. Saccharomyces cerevisiae. Higher eukaryotic cells include insect and vertebrate cells, particularly mammalian cells. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of Drosophila $p70^{S6K}$-encoding nucleic acid to form Drosophila $p70^{S6K}$ The precise amounts of DNA encoding Drosophila $p70^{S6K}$ may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby Drosophila $p70^{S6K}$ encoded by the DNA is expressed. The composition of suitable media is known to those in the art, so that they can be readily prepared. Suitable culturing media are also commercially available.

The polypeptide according to the invention may advantageously be expressed in insect cell systems. Insect cells suitable for use in the method of the invention include, in principle, any lepidopteran cell which is capable of being transformed with an expression vector and expressing heterologous proteins encoded thereby. In particular, use of the Sf cell lines, such as the *Spodoptera frugiperda* cell line IPBL-SF-21 AE (Vaughn et al., (1977) In Vitro, 13, 213–217) is preferred. The derivative cell line Sf9 is particularly preferred. However, other cell lines, such as *Tricoplusia ni*368 (Kurstack and Marmorosch, (1976) Invertebrate Tissue Culture Applications in Medicine, Biology and Agriculture. Academic Press, New York, USA) may be employed. These cell lines, as well as other insect cell lines suitable for use in the invention, are commercially available (e.g. from Stratagene, La Jolla, Calif., USA).

As well as expression in insect cells in culture, the invention also comprises the expression of heterologous proteins in whole insect organisms. The use of virus vectors such as baculovirus allows infection of entire insects, which are in some ways easier to grow than cultured cells as they have fewer requirements for special growth conditions. Large insects, such as silk moths, provide a high yield of heterologous protein. The protein can be extracted from the insects according to conventional extraction techniques.

Expression vectors suitable for use in the invention include all vectors which are capable of expressing foreign proteins in insect cell lines. In general, vectors which are useful in mammalian and other eukaryotic cells are also applicable to insect cell culture. Baculovirus vectors, specifically intended for insect cell culture, are especially preferred and are widely obtainable commercially (e.g. from Invitrogen and Clontech). Other virus vectors capable of infecting insect cells are known, such as Sindbis virus (Hahn et al., (1992) PNAS (USA) 89, 2679–2683). The baculovirus vector of choice (reviewed by Miller (1988) Ann. Rev. Microbiol. 42, 177–199) is *Autographa californica* multiple nuclear polyhedrosis virus, AcMNPV.

Typically, the heterologous gene replaces at least in part the polyhedrin gene of AcMNPV, since polyhedrin is not required for virus production. In order to insert the heterologous gene, a transfer vector is advantageously used. Transfer vectors are prepared in *E. coli* hosts and the DNA insert is then transferred to AcMNPV by a process of homologous recombination.

Expression systems encoding *Drosophila* $p70^{S6K}$ are useful for the study of $p70^{S6K}$ activity, particularly in the context of transgenic *Drosophila* flies. Preferred is a system in which $p70^{S6K}$ expression has been attenuated, particularly where this is achieved by means of transposon insertion. It has been determined, for instance, that mutant fs(3)07084 (Karpen, G. H. & Spradling A. C. Genetics 132, 737–753 (1992); Spradling, A. C. et al. Proc. Natl. Acad. Sci. USA 92, 10824–10830 (1995)) contains a P-element insertion in the 5' region of the *Drosophila* $p70^{S6K}$ gene. Sequencing of the mutant shows that the insertion is localised 41 base pairs upstream of the *Drosophila* $p70^{S6K}$ AUG initiator codon.

Mutant files according to the invention have impaired $p70^{S6K}$ expression. Homozygotes for the fs(3)07084 mutation show impaired and/or delayed oogenesis, due to low levels of $p70^{S6K}$ production as a result of attenuation of gene transcription by the transposon insertion. Mutations in which $p70^{S6K}$ expression is entirely eliminated are lethal in homozygous form.

Expression mutants of *Drosophila* $p70^{S6K}$, particularly those in which expression is severely attenuated but not eliminated, are useful for the study of $p70^{S6K}$ activity. They show increased sensitivity to modulated interaction of putative upstream signalling agents with the regulatory domains of $p70^{S6K}$, as well as modification of the downstream targets predicted to mediate its biological response. Thus, the invention also provides a method for assessing the ability of an agent to target *Drosophila* $p70^{S6K}$ activity comprising exposing a *Drosophila* $p70^{S6K}$ mutant as described herein to the agent, and judging the effect of the biological activity of $p70^{S6K}$.

In accordance with yet another embodiment of the present invention, there are provided antibodies specifically recognising and binding to *Drosophila* $p70^{S6K}$. For example, such antibodies may be generated against the *Drosophila* $p70^{S6K}$ having the amino acid sequences set forth in SEQ ID No. 2. Alternatively, *Drosophila* $p70^{S6K}$ or *Drosophila* $p70^{S6K}$ fragments (which may also be synthesised by in vitro methods) are fused (by recombinant expression or an in vitro peptidyl bond) to an immunogenic polypeptide and this fusion polypeptide, in turn, is used to raise antibodies against a *Drosophila* $p70^{S6K}$ epitope.

Anti-*Drosophila* $p70^{S6K}$ antibodies are recovered from the serum of immunised animals. Alternatively, monoclonal antibodies are prepared from cells in vitro or from in vivo immunised animals in conventional manner.

The antibodies of the invention are useful for studying *Drosophila* $p70^{S6K}$ localisation, screening of an expression library to identify nucleic acids encoding *Drosophila* $p70^{S6K}$ or the structure of functional domains, as well as for the purification of *Drosophila* $p7^{S6K}$, and the like.

Antibodies according to the invention may be whole antibodies of natural classes, such as IgE and IgM antibodies, but are preferably IgG antibodies. Moreover, the invention includes antibody fragments, such as Fab, $F(ab')_2$, Fv and ScFv. Small fragments, such Fv and ScFv, possess advantageous properties for diagnostic and therapeutic applications on account of their small size and consequent superior tissue distribution.

The antibodies according to the invention are especially indicated for diagnostic and therapeutic applications. Accordingly, they may be altered antibodies comprising an effector protein such as a toxin or a label. Especially preferred are labels which allow the imaging of the distribution of the antibody at the site of infection in vivo, or in a biopsy. Such labels may be radioactive labels or radioopaque labels, such as metal particles, which are readily visualisable within the body of a patient. Moreover, they may be fluorescent labels or other labels which are visualisable on tissue samples removed from patients.

Recombinant DNA technology may be used to improve the antibodies of the invention. Thus, chimeric antibodies may be constructed in order to decrease the immunogenicity thereof in diagnostic or therapeutic applications. Moreover, immunogenicity may be minimised by humanising the antibodies by CDR grafting [see European Patent Application 0 239 400 (Winter)] and, optionally, framework modification [see international patent application WO 90/07861 (Protein Design Labs)].

Antibodies according to the invention may be obtained from animal serum, or, in the case of monoclonal antibodies or fragments thereof, produced in cell culture. Recombinant DNA technology may be used to produce the antibodies according to established procedure, in bacterial or preferable in mammalian cell culture. The selected cell culture system preferably secretes the antibody product.

Therefore, the present invention includes a process for the production of an antibody according to the invention comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding the antibody, and isolating said antibody.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. fetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The cell culture supernatants are screened for the desired antibodies, preferentially by immunofluorescent staining of cells expressing $Drosophila\ p70^{S6K}$, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-)affinity chromatography, e.g. affinity chromatography with $Drosophila\ p70^{S6K}$ protein covalently attached to a solid support or with Protein-A.

The invention further concerns hybridoma cells secreting the monoclonal antibodies of the invention. The preferred hybridoma cells of the invention are genetically stable, secrete monoclonal antibodies of the invention of the desired specificity and can be activated from deep-frozen cultures by thawing and recloning.

The invention also concerns a process for the preparation of a hybridoma cell line secreting monoclonal antibodies directed $Drosophila\ p70^{S6K}$, characterised in that a suitable mammal, for example a Balb/c mouse, is immunised with purified $Drosophila\ p70^{S6K}$ protein, an antigenic carrier containing purified $Drosophila\ p70^{S6K}$ or with cells bearing $Drosophila\ p70^{S6K}$, antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with cells bearing $Drosophila\ p70^{S6K}$ are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting subcutaneously and/or intraperitoneally between $10^7$ and $10^8$ cells which express $Drosophila\ p70^{S6K}$ containing a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

The invention also concerns recombinant DNAs comprising an insert coding for a heavy chain variable domain and/or for a light chain variable domain of antibodies directed to the extracellular domain of $Drosophila\ p70^{S6K}$ as described hereinbefore. By definition such DNAs comprise coding single stranded DNAS, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed $Drosophila\ p70^{S6K}$ can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly $E.\ coli$, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

The invention therefore also concerns recombinant DNAs comprising an insert coding for a heavy chain murine variable domain of an antibody directed Drosophila p70$^{S6K}$ fused to a human constant domain γ, for example γ1, γ2, γ3 or γ4, preferably γ1 or γ4. Likewise the invention concerns recombinant DNAs comprising an insert coding for a light chain murine variable domain of an antibody directed to Drosophila p70$^{S6K}$ fused to a human constant domain κ or λ, preferably κ.

In another embodiment the invention pertains to recombinant DNAs coding for a recombinant DNA wherein the heavy chain variable domain and the light chain variable domain are linked by way of a DNA insert coding for a spacer group, optionally comprising a signal sequence facilitating the processing of the antibody in the host cell and/or a DNA coding for a peptide facilitating the purification of the antibody and/or a DNA coding for a cleavage site and/or a DNA coding for a peptide spacer and/or a DNA coding for an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

The invention is described hereinbelow, for the purposes of illustration only, in the following examples.

Materials and Methods

Nucleic Acid Isolation and Hybridisation.

Genomic DNA and total RNA are isolated from adult Canton S flies as previously described (Stewart, M. J. & Denell, R. (1993) Mol. Cell. Biol. 13, 2524–2535) DNA and RNA are fractionated on a 0.8% agarose gel in 0.5× TBE or a 0.7% agarose gel containing 2.2 M formaldehyde, 50 mM MOPS, and 1 mM EDTA, respectively, transferred to Hybond N membranes (Amersham) and hybridised as described. Final washes are carried out twice for 30 minutes at 68° C. in 0.1× SSPE; 0.1% SDS. DNA probes are labelled using a random priming kit (Boehringer) to a specific activity of >109 cpm per ug.

cDNA Library Screening and Sequencing.

Genomic and cDNA libraries are screened employing hybridisation and washing conditions as above. A fragment of the rat p70$^{S6K}$ 2B4 clone encompassing nucleotides 42 to 431 (Reinhard, C., et al. (1992) Proc. Natl. Acad. Sci. USA 89, 4052–4056) is used to screen a Drosophila genomic library constructed from Dr(2R)SB1/CyO flies (Baumgartner, S., et al. (1987) Genes & Dev. 1, 1247–1267). Partial sequence data from genomic clones revealed a 0.9 kb XhoI fragment with open reading frames showing homology to the mammalian p70$^{S6K}$ catalytic domain. This fragment is used to screen a oligo-dT primed Canton S embryonic cDNA library in the UniZap XR vector (Stratagene). Analysis of 11 independent cDNAs revealed all are internally primed from a polyadenine stretch at base 2062 which also occurs in the genomic sequence. Thus, a genomic clone containing the ORF extending 3' of these adenines is used to screen the cDNA library mentioned above as well as a random primed Canton S embryonic cDNA library in the Stratagene lambda ZAPII vector (provided by Dr. Carl Thummel). A variable number of adenine residues is noted in clones from the random primed library at position 2062, most likely arising due to enzyme stuttering during cDNA synthesis. Overlapping clones make up a transcription unit of 3.6 kb with multiple consensus polyadenylation signals, two of which are utilised in recovered clones. Comparison of genomic and cDNA sequences 3' of base 2062 revealed two apparent strain polymorphisms resulting in substitution of Leu for Phe632 and insertion of three Glu residues at amino acid 567 in the genomic sequence. DNA sequencing is carried out using specific oligonucleotide primers and the Bst (Bio-Rad) and Sequenase version 2.0 (U.S. Biochemical Corp.) systems. The Drosophila p70$^{S6K}$ DNA sequence is submitted to GenBank/EMBL DNA Data Bank of Japan under the accession number U 66562.

Plasmid Constructs and Cell Transfections.

A construct containing the entire Drosophila p70$^{S6K}$ coding region is generated by fusing a HindIII/Kpnl genomic fragment to the HindIII site at base 2026 within the cDNA and a Kpnl site within the polylinker of a cloning vector. PCR mutagenesis employing PFU polymerase and specific oligonucleotides is used to insert a myc-epitope tag at the amino-terminus of the Drosophila p70$^{S6K}$ cDNA. This construct is confirmed by sequencing and subcloned into the vector pBD$_{1119}$ under the control of the alpha tubulin promoter (Theurkauf, W. E., et al. (1986) Proc. Natl. Acad. Sci. USA 83, 8477–8481) and transfected into Schneider line 2 (S2) cells using a modified calcium phosphate-precipitation method (Chen, C. A. & Okayama, H. (1988) Biotechniques 6, 632–638).

Antibody Production and Immunoblot Analysis.

The peptide MADVSDPSELFDLELHDLEY (SEQ ID NO:1) coupled to a carboxy terminal tyrosine is conjugated to Keyhole Limpet hemocyanin and used to produce a rabbit polyclonal antiserum (Neosystem). The peptide is coupled to CNBr activated Sepharose (Pharmacia) and used to affinity purify specific antibodies after ammonium sulphate precipitation of the antiserum (Harlow, H. A. & Lane, D. (1988) Antibodies—A laboratory manual; Cold Spring Harbor Lab. Press, Cold Spring Harbor, N.Y.). Affinity-purified antibody (D20 antibody) is diluted 1/1000 for Western blot analysis. Extracts from S2 cells, prepared as described (Tuta, M., et al. (1989) Cell 57, 817–824), are subjected to Western blot analysis with the D20 antibody. Blots are decorated with a horse radish peroxidase conjugated anti-rabbit secondary antibody and bands detected using the ECL system (Amersham Corp).

Kinase Assays and Immunoprecipitations.

Cell extracts are prepared and Drosophila p70$^{S6K}$ activity is measured as previously described (28) or following immunoprecipitation (Lane, H. A., et al. (1992) EMBO J 11, 1743–1749) with the D$_{20}$ antibody (2.5 μg).

Mono Q Chromatography.

S2 cells are plated at 5'107 cells per 15 cm dish in Schneider's medium supplemented with antibiotic and 10% foetal calf serum. After 24 h, cells are changed to Schneider's medium without serum and after an additional 36 h, 5 plates of cells are treated with 100 μM cycloheximide for two hours with or without pretreatment with 20 nm rapamycin for 15 min. Cell extracts are prepared by dounce homogenisation in Extraction buffer lacking PNPP as described in Reinhard et al., above. Briefly, each extract is centrifuged for 30 min at 3×105 g, filtered through a 0.2 μm membrane (Millipore), and applied at a flow rate of 0.5 ml per min to a 1 ml Mono Q column (Pharmacia) equilibrated in Buffer F (Kozma, S. C., et al. (1989) EMBO J 8, 4125–4132). The column is washed with 10 ml of Buffer F, developed at 0.5 ml per min with a 30 ml gradient from 0–0.5 M NaCl in the same buffer, and each fraction is diluted 20-fold and assayed for kinase activity. Factions 16–19 are concentrated on 100 µl of FFQ Sepharose and eluted with 300 µl of 0.5 M NaCl in Buffer F.

Expression Mutant Analysis.

Genomic DNA flanking the left insertion point of the P element in fs(3)07084 was cloned by plasmid rescue as described (Pirrotta, V. in *Drosophila*: a practical approach (ed. D. B. Roberts) IRL Press, Oxford, UK, 1986)) and sequenced using an oligonucleotide primer based on the P element inverted repeats (Rubin, G. M. & Spradling, A. C. *Drosophila* Nucleic Res. 11, 6341–6351 (1983)) and *Drosophila* p70$^{S6K}$ specific primers. Genomic DNA was isolated and subjected to Southern blot analysis as previously described (Lindsley, D. J. & Zimm, G. G. Academic Press, San Diego, Calif. USA. (1992)). Canton S was used as the wild type strain. All markers and Balancer chromosomes are as described (Wieschaus, E. & Nesslein-Volhard, C. in Drosphila: a practical approach (ed D. B. Roberts) IRL Press, Oxford, UK. 1986)).

Eggs were collected and mounted in Hoyers mountant as described. Microscopy was done with a Zeiss Axiophot.

Ovaries were dissected from 3–4 day old Canton S (wild type) or fs(3)*Drosophila* p70$^{S6K}$/fs(3)*Drosophila* p70$^{S6K}$ females, immediately frozen in N2 and then stored at −800° C. Total protein was extracted by dounce homogenisation of ovaries in extraction buffer (Lane, H. A. et al. EMBO J. 11, 1743–1749 (1992)) containing in addition 25 µm leupeptin, 10 mm EDTA, 10 mm EGTA and 5 mg/ml aprotinin. Proteins were separated by 12% SDS-PAGE and subjected to Western blot analysis with a 1/50 dilution of D20 antibody followed by an HRP conjugated secondary antibody and bands were visualised using ECL (Boehringer). Total RNA was isolated from ovaries and Northern blot analysis performed. For rRNA analysis, eggs were collected every two hr. and kept on ice in PBS until 30 eggs were accumulated, approximately 6 hr. The eggs were then gently pelleted by centrifugation, the supernatant removed, 200 µl of lysis buffer 30 containing 0.1% SDS was added, the eggs homogenised in an Eppendorf tube with a Pellet Pestle (Kontes), the extract heated to 60° C. for 1 min., followed by centrifugation at maximum speed for 15 min. on an Eppendorf centrifuge to remove insoluble material, and 150 µl of the extract loaded on a 4 ml isokinetic sucrose gradient and analysed at A260 as previously described (Thomas, G. et al. Exp. Cell. Res. 108, 253–258 (1977)). The amount of RNA present was calculated from the area of the 28S and 18S rRNA peaks.

Results

*Drosophila* p70$^{S6K}$.

To identify cDNA clones encoding the *Drosophila* p70$^{S6K}$ homologue, *Drosophila* genomic clones are first isolated by hybridisation with a rat p70$^{S6K}$ cDNA probe, and are then used to screen *Drosophila* cDNA libraries (see Materials & Methods). A number of overlapping cDNA fragments are isolated which, when aligned, represent a transcription unit of 3.6 kb. Conceptual translation of this cDNA, termed *Drosophila* p70$^{S6K}$, shows it contains a single large open reading frame encoding a protein of 637 amino-acids with a predicted M. W. 73 kD, containing all the conserved motifs found in Ser/Thr kinases. Northern blot analysis of total RNA revealed three transcripts of 2.8 kb, 3.7 kb and 5.0 kb in size. The 2.8 kb transcript is significantly more abundant in females than males, whereas in males the 3.7 kb transcript is most abundant. The size of the hypothetical *Drosophila* p70$^{S6K}$ cDNA is consistent with the 3.7 kb message seen by Northern blot analysis. Both the 2.8 kb and 5.0 kb transcripts may represent either alternatively-spliced transcripts or mRNAs which utilise distinct polyadenylation signals (see Materials and Methods). All three transcripts appear specific for the *Drosophila* p70$^{S6K}$ gene, as a probe derived from outside of the *Drosophila* p70$^{S6K}$ catalytic domain detected identical transcripts (data not shown). Although multiple transcripts may be indicative of a gene family, the majority of *Drosophila* genes are single copy and the mammalian p70$^{S6K}$ is represented by a single gene (Reinhard, C., et al. (1992) Proc. Natl. Acad. Sci. USA 89, 4052–4056). To determine the number of *Drosophila* p70$^{S6K}$ gene copies, a high stringency genomic Southern blot analysis is carried out. Only three restriction fragments are detected in XhoI-digested genomic DNA when *Drosophila* p70$^{S6K}$ cDNA is employed as a probe, consistent with the presence of two XhoI sites within the *Drosophila* p70$^{S6K}$ cDNA. Furthermore, double digestion of genomic DNA with EcoRI and XhoI does not reveal additional fragments. Depending on the specific restriction enzyme used, the *Drosophila* p70$^{S6K}$ cDNA hybridised to only two or three genomic DNA fragments indicating an approximate size of 15 kb for the gene excluding potential regulatory regions. These results argue for a single copy gene and are consistent with *Drosophila* p70$^{S6K}$ representing the unique member of this family.

Conservation of Regulatory Domains.

Analysis of the predicted *Drosophila* p70$^{S6K}$ amino-acid sequence shows 57% overall identity to the mammalian p70$^{S6K}$ sequence with the highest homology in the catalytic domain where the identity is 78% and the similarity is 86%. The acidic amino-terminal domain of mammalian p70$^{S6K}$ confers rapamycin sensitivity on the kinase (Weng, Q-P., et al. (1995) Mol. Cell. Biol. 15, 2333–2340; Dennis, P. B., et al. (1996)). In *Drosophila* p70$^{S6K}$ this domain is also highly acidic, displaying 55% similarity with its mammalian counterpart, suggesting it may play an equivalent role in *Drosophila* p70$^{S6K}$. Immediately adjacent to the catalytic domain, *Drosophila* p70$^{S6K}$ contains a 68 amino acid long sequence which has a striking 72% identity with its mammalian homologue. In mammalian p70$^{S6K}$ this domain couples the catalytic and autoinhibitory domains, and is termed the linker region. It has recently been noted that this region is conserved in many members of the second messenger subfamily of Ser/Thr kinases and may play a critical role in regulating kinase activity (Pearson, R. B., et al (1995) EMBO J. 14, 5279–5287). This linker region is immediately followed by the putative autoinhibitory domain (see below) which contains four Ser/Thr-Pro sites whose phosphorylation is thought to relieve the inhibitory impact of this domain as well as contribute to full kinase activation. Consistent with this model it is previously shown that peptides covering this domain, residues 400 to 432, inhibit kinase activity in the low µM range (Price, D. J., et al. (1991) J. Biol. Chem. 266, 16281–16284; Flotow, H. & Thomas, G. (1992) J. Biol. Chem. 267, 3074–3078). Strikingly, in *Drosophila* p70$^{S6K}$ the sequence R417SPRRTPR425 (SEQ ID NO:4) immediately following the linker region is very similar in context to a piece of the mammalian autoinhibitory domain, R410SPRRFIGSPR419 (SEQ ID NO:5). Although this peptide only represents a fragment of the autoinhibitory domain found in p70$^{S6K}$, in recent studies it is defined as the sequence within the larger peptide which is responsible for exerting the inhibitory effect on p70$^{S6K}$. Thus in *Drosophila* p70$^{S6K}$ this sequence may be involved in auto-regulation of kinase activity in a manner similar to that predicted in mammalian p70$^{S6K}$. The final stretch of amino acids, residues 425 to 637, display no significant homology with the mammalian p70$^{S6K}$ nor with known proteins from database searches, indicating this carboxy-terminal domain is unique to *Drosophila* p70$^{S6K}$. However, this domain contains a highly basic lysine residues beginning at amino-acid 525, which is separated by thirty five amino acids from a long stretch of acidic amino acids nearer the carboxy-terminus. Given that there is no detectable nuclear targeting sequence in the *Drosophila* p70$^{S6K}$ equivalent to that found in the mammalian p85s6k isoform, it would be of interest to test whether these sequences perform a similar function in *Drosophila* p70$^{S6K}$.

*Drosophila* p70$^{S6K}$ Expression.

To determine whether the *Drosophila* p70$^{S6K}$ cDNA encodes a protein product equivalent to the endogenous protein, *Drosophila* Schneider line 2 (S2) cells are transiently transfected with a *Drosophila* p70$^{S6K}$ construct containing a myc epitope-tag at its amino-terminus (Materials and Methods). Following transfection, protein products are visualised by Western blot analysis, employing the monoclonal antibody 9E10 (Ming, X. F., et al. (1994) Nature 371, 426–429). A protein band with Mr 70 k is specifically detected in extracts from transiently transfected cells, but is absent in extracts from control cells. To determine whether an equivalent protein could be detected in extracts of S2 cells, a rabbit polyclonal antibody (D20) is generated against a peptide representing amino acids 1–19 of the *Drosophila* p70$^{S6K}$ amino-terminus (Materials and Methods). This antibody specifically recognises an endogenous protein of Mr 70 k in S2 cells which co-migrates with the kinase produced ectopically from transient transfection of the cDNA in S2 cells that is detected with either the D20 antiserum or the 9E10 antibody. Longer exposures of the film do not reveal additional bands that might be suggestive of an isoform equivalent to the mammalian p85s6k (Reinhard, C., et al. (1994) EMBO J. 13,1557–1565). Preincubation of the D20 antiserum with the antigenic peptide prevents binding to *Drosophila* p70$^{S6K}$. Thus, the *Drosophila* p70$^{S6K}$ cDNA encodes a protein which is antigenically equivalent to a *Drosophila* protein which migrates at a similar molecular weight.

S6 Kinase Activity and Sensitivity to Rapamycin.

Activation of the rat p70$^{S6K}$ is associated with phosphorylation of ten residues (Pearson, R. B., et al. (1995) EMBO J. 14, 5279–5287), five of which are conserved in *Drosophila* p70$^{S6K}$. By mutational analysis, three of the ten sites, T229, S371 and T389, have been argued to be critical for p70$^{S6K}$ activation. These sites are conserved in *Drosophila* p70$^{S6K}$ as T238, S380, and T398. In addition the principal target of rapamycin-induced p70$^{S6K}$ dephosphorylation and inactivation is T389, with T229 acting as a secondary target. However, for rapamycin to exert this inhibitory response on mammalian p70$^{S6K}$, the macrolide requires the acidic residues at the amino-terminus. As discussed above this may be a feature also conserved in *Drosophila* p70$^{S6K}$. To examine whether S2 cells contain S6 kinase activity and if so, whether this activity is sensitive to rapamycin, mammalian 40S ribosomes are incubated with extracts from S2 cells treated with cycloheximide, an agent known to activate mammalian p70$^{S6K}$ (Kozma, S. C., et al. (1989) EMBO J 8, 4125–4132; Mukhopadhayay, N. K., et al. (1992) J. Biol. Chem. 267, 3325–3335), in the absence or presence of the macrolide. Mammalian 40S ribosomes are employed in these assays as they are found to be as good a substrate as their *Drosophila* counterparts (data not shown). Cycloheximide treatment of S2 cells increased S6 kinase activity 2.2 fold over basal levels and rapamycin pretreatment prevented this increase, reducing activity below basal levels. However, a significant amount of rapamycin insensitive kinase activity towards S6 is still apparent.

To distinguish between these rapamycin sensitive and insensitive S6 kinase activities and to determine whether either represented *Drosophila* p70$^{S6K}$, extracts from cycloheximide-stimulated S2 cells, pretreated with or without rapamycin, are fractionated by Mono Q chromatography. The fractions eluted from the Mono Q column are monitored by A280 and subjected to an in vitro S6 kinase assay. Two peaks of S6 kinase activity emerged from the column. The first peak contained less S6 kinase activity, eluted at 0.13 M NaCl and is rapamycin insensitive. The second peak of activity eluted at 0.29 M NaCl, contained approximately 15-fold more S6 kinase activity, and is completely abolished by rapamycin pretreatment. To assess whether the S6 kinase activity in this peak is attributable to *Drosophila* p70$^{S6K}$, we used FFQ Sepharose to concentrate the fractions 16 to 18 containing the rapamycin sensitive S6 kinase activity. The concentrated samples from cells treated with cycloheximide either in the absence or presence of rapamycin pretreatment, are either immunoprecipitated and assayed for S6 kinase activity or analysed on Western blots employing the D20 antibody. The antibody specific for *Drosophila* p70$^{S6K}$ immunoprecipitated S6 kinase activity from the sample stimulated with cycloheximide, but no activity could be detected from the sample pretreated with rapamycin prior to the addition of cycloheximide. Western blot analysis of these fractions revealed a slower electrophoretic mobility on SDS PAGE for the active *Drosophila* p70$^{S6K}$ as compared to the inactive kinase. This altered electrophoretic mobility is similar to the mobility shift induced by phosphorylation of the mammalian p70$^{S6K}$, an effect that is ablated by rapamycin treatment. Thus, cycloheximide treatment induces the activation of *Drosophila* p70$^{S6K}$, which is apparently regulated by phosphorylation and is rapamycin sensitive.

Expression Mutant.

We have localised *Drosophila* p70$^{S6K}$ by in situ hybridisation to chromosome position 64F1–3 (data not shown) with the aim of determining whether mutants existed in the gene and, if so, whether they exhibit a phenotype consistent with the presumptive role of p70$^{S6K}$ in ribosome biogenesis. A search of FlyBase11 revealed that several P element insertion mutants map to this location. By RFLP analysis one of these mutants, fs(3)07084 (Karpen, G. H. & Spradling A. C. Genetics 132, 737–753 (1992); Spradling, A. C. et al. Proc. Natl. Acad. Sci. USA 92,10824–10830 (1995)) is found to contain a P element in the 5' region of the *Drosophila* p70$^{S6K}$ gene. Sequencing of flanking genomic DNA, localised the P element insertion to 41 base pairs upstream of the *Drosophila* p70$^{S6K}$ AUG initiator codon, strongly implying that the mutation would disrupt *Drosophila* p70$^{S6K}$ expression (see below).

Homozygous flies eventually eclose as adults, however their final number is roughly a quarter of the expected value (Table 1A). These flies emerge as adults after an average delay of approximately four days as compared with either their heterozygous or wild type counterparts (Table 1 A). This represents a relative 30% reduction in the rate of development as compared with heterozygous or wild type flies (Table 1A). When homozygous mutant males are crossed with wild type females there is no discernible effect on development, whereas eggs from a reciprocal cross failed to complete embryogenesis. Analysis of ovaries of 2 to 3 day old homozygous females appear mature and exhibit no obvious defects (data not shown). However, homozygous mutant females lay an average of five times less eggs than either heterozygous or wild type females (Table 1B). These eggs display aberrant, antler-like, dorsal appendages which do not complete development relative to dorsal appendages of wild type eggs. Consistent with this finding the dorsal-most follicle cells have not elongated and the eggs appear comparatively smaller, exhibiting a short egg phenotype. The dorsal appendage is an extension of the chorion, and though synthesised by the follicle cells, is dependent on the growth and elongation of the egg chamber that takes place between stages 11–13 of oogenesis (Spradling, A. C. in The Development of *Drosophila melanogaster* (eds Bate, M. & Martinez Arias, A.) Vol.1, Cold Spring Harbor Laboratory Press, Cold Spring Harbor, 1993). This step of development immediately follows the dramatic upregulation of ribosome biogenesis, stages 8–10, which is required for the completion of oogenesis (Mermod, J-J. et al. Development Bio. 57, 393–402 (1977)). Indeed many of the gene products required for the massive growth of the oocyte between stages 11–13 are produced in large amounts during stage 10B.

A P element mobilisation scheme led to recovery of the wild type phenotype, therefore we have termed this gene *Drosophila* $p70^{S6K}$ fs(3)07084. This finding suggested that the P element insertion led to a reduction of kinase expression, similar to that reported for other genes in which the P element is inserted in the 5' UTR of the gene. To examine this possibility we compared the levels of *Drosophila* $p70^{S6K}$ from ovaries of wild type flies with those found in heterozygous and homozygous mutants by western blot analysis employing a specific antibody. The results show that the amount of *Drosophila* $p70^{S6K}$ is notably reduced in heterozygous females and that it is not detectable in homozygous mutants, suggesting that this mutant is a null for *Drosophila* $p70^{S6K}$. However, Northern blot analysis of total RNA from ovaries of homozygous mutant females, employing the *Drosophila* $p70^{S6K}$ cDNA as a probe, revealed three transcripts. The relative amounts of these transcripts are significantly less than in wild type females and they migrate with a relative increased molecular weight. This difference in size suggests that the mutant transcripts initiate transcription from within the P element. Genetic support for *Drosophila* $p70^{S6K}$ presence comes from P element excisions in which the transposon is incorrectly removed, such that no viable homozygous flies are recovered. In addition, heterozygous females flies carrying *Drosophila* $p70^{S6K}$ fs(3)07084 on one allele and a deficiency spanning the *Drosophila* $p70^{S6K}$ on the other allele, DF(3L) ZN4711, lay even less nonviable eggs than homozygous *Drosophila* $p70^{S6K}$ fs(3)07084 females. Thus the P element insertion appears to strongly suppress expression of *Drosophila* $p70^{S6K}$, allowing the observation of the phenotype, which would not have been perceived in the absence of the gene.

The slower rate of development observed for homozygous *Drosophila* $p70^{S6K}$ fs(3)07084 flies as well as the exhibited decrease in fertility and egg size are characteristic of Minute and bobbed mutations. The Minute loci comprise a class of approximately fifty haplo-insufficent loci, which are speculated to affect ribosomal proteins (Vaslet, C. A. et al. Nature 285, 674–676 (1980)). To date, five Minute loci have been demonstrated to represent deletions of ribosomal proteins of both subunits (Vaslet, C. A. et al. Nature 285, 674–676 (1980)). The bobbed mutants affect rRNA geneS2o with the severity of the phenotype proportional to the number of deleted functional genes (Shermoen, A. W. & Kiefer, B. I. Cell 4, 275–280 (1975)). Flies mutant for either of these two classes of genes display reduced fertility, exhibit a retarded rate of development, and in some cases display small slender bristles. Though the latter phenotype is not observed in *Drosophila* $p70^{S6K}$ fs(3)07084 homozygotes, the other characteristics are highly similar, indicating a reduction in the rate of translation due to a decrease in ribosome content. Stages 8–10 of *Drosophila* oogenesis are thought to represent the most spectacular example of ribosome synthesis of any tissue at any time of development, ie most of the $5 \times 10^{10}$ ribosomes produced in the nurse cells and oocyte are generated within this period (Kay, M. A. & Jacobs-Lorena, M. TIG 3, 347–351 (1987)). These ribosomes are required for the dramatic growth and development of the oocyte at the end of oogenesis. Accompanying this event is the selective translational upregulation of ribosomal protein mRNA transcripts, many of which contain a 5'TOP5. Given the putative role of the $p70^{S6K}$ in mediating the selective upregulation of these mRNAs at the translational level, we reasoned that the *Drosophila* $p70^{S6K}$ fs(3)07084 phenotype may be explained by a reduction in ribosome content. To examine this possibility, we isolated total ribosomes from eggs laid by wild type or homozygous mutant females and scored for the amount of rRNA as a measure of ribosome content. Quantitation of these results revealed a striking 40% reduction in both 40S and 60S subunits in eggs derived from mutant females versus their wild type counterparts.

The observed phenotypic manifestations of reduced *Drosophila* $p70^{S6K}$ expression are consistent with the predicted role of the kinase in protein synthesis (Jefferies, H. B. J. & Thomas, G. in Translational Control (eds Hershey, J. W. B. Mathews, M. B. & Sonenberg, N.) Vol. 1, Cold Spring Harbor Press, Cold Spring Harbor, 1995)) and emphasise the importance of the $p70^{S6K}$ signalling pathway during cell growth and development. The function of the $p70^{S6K}$ signalling pathway in these processes is beginning to be elucidated5, as are the identity of putative upstream signalling molecules (Downward, J. Nature 376, 553–554 (1995)). The availability of a mutant which cripples but does not ablate this pathway will prove immensely valuable in unravelling the functional importance of potential regulatory domains within the kinase and the relative importance of downstream targets predicted to mediate its biological responses.

TABLE 1

A. Offspring of heterozygous matings

| Flies | Number of Adult Flies | Eclosion |
| --- | --- | --- |
| homozygotes | 93 (357 expected) | 16.3 days |
| heterozygotes | 715 | 12.7 days |

B. Eggs Laid

| Flies | Eggs per day | Eggs counted |
| --- | --- | --- |
| wild-type | 37.7 | 2208 |
| heterozygotes | 40.4 | 5630 |
| homozygotes | 8.52 | 1388 |

What is claimed is:

1. $p70^{S6K}$ isolated from *Drosophila* consisting of the amino acid sequence set forth in SEQ ID NO:2.

2. $p70^{S6K}$ isolated from *Drosophila* comprising the amino acid sequence set forth in SEQ ID NO: 2.

* * * * *